(12) United States Patent
Ashraf (10) Patent No.: US 7,513,969 B2
(45) Date of Patent: Apr. 7, 2009

(54) METHOD FOR PRODUCING A CORRUGATED STRETCH LAMINATE WITH A FREE FORMED PRINTED ELASTIC MEMBER

(75) Inventor: Arman Ashraf, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 414 days.

(21) Appl. No.: 10/966,475

(22) Filed: Oct. 15, 2004

(65) Prior Publication Data

US 2006/0083893 A1 Apr. 20, 2006

(51) Int. Cl.
*A61F 13/15* (2006.01)

(52) U.S. Cl. .................. 156/163; 156/164; 156/229; 156/244.11

(58) Field of Classification Search .......... 156/242, 156/160, 245, 164, 163, 161, 229, 244.11; 264/167, DIG. 70
See application file for complete search history.

(56) References Cited

U.S. PATENT DOCUMENTS

| | | | |
|---|---|---|---|
| 1,974,209 A * | 9/1934 | Fowler ................ | 156/242 |
| 2,957,200 A * | 10/1960 | Pufahl et al. ......... | 264/DIG. 70 |
| 3,085,292 A * | 4/1963 | Kindseth ............ | 264/167 |
| 3,848,594 A | 11/1974 | Buell | |
| 3,860,003 A | 1/1975 | Buell | |
| 4,329,309 A * | 5/1982 | Kelly ................ | 264/167 |
| 4,606,964 A * | 8/1986 | Wideman ............ | 156/164 |
| 4,626,305 A * | 12/1986 | Suzuki et al. ......... | 156/164 |
| 4,662,875 A | 5/1987 | Hirotsu et al. | |
| 4,846,815 A | 7/1989 | Scripps | |
| 4,847,134 A | 7/1989 | Fahrenkrug et al. | |
| 4,894,060 A | 1/1990 | Nestegard | |
| 4,946,527 A | 8/1990 | Battrell | |
| 5,151,092 A | 9/1992 | Buell et al. | |
| 5,221,274 A | 6/1993 | Buell et al. | |
| 5,422,172 A | 6/1995 | Wu | |
| 5,554,145 A | 9/1996 | Roe et al. | |
| 5,569,234 A | 10/1996 | Buell et al. | |
| 5,580,411 A | 12/1996 | Nease et al. | |
| 6,004,306 A | 12/1999 | Robles et al. | |
| 6,432,098 B1 | 8/2002 | Kline et al. | |
| 2003/0088228 A1 | 5/2003 | Desai et al. | |
| 2003/0091807 A1 | 5/2003 | Desai et al. | |

(Continued)

FOREIGN PATENT DOCUMENTS

EP 0 672 516 A 9/1995

(Continued)

OTHER PUBLICATIONS

U.S. Appl. No. 60/557,288, filed Mar. 29, 2004, Fred Desai.

(Continued)

*Primary Examiner*—Jeff H Aftergut
(74) *Attorney, Agent, or Firm*—Charles E. Matson; Eric T. Addington (57) ABSTRACT

A process for making a corrugated stretch laminate comprising the steps of delivering a first elastomeric composition to a print device so as to form an elastic member; removing an elastic member from the print device; elongating the elastic member in a first direction; joining the elastic member to a first substrate; and allowing the elastic member to recovery to form said corrugated stretch laminate.

17 Claims, 5 Drawing Sheets

U.S. PATENT DOCUMENTS

| | | |
|---|---|---|
| 2004/0005835 A1 | 1/2004 | Zhou et al. |
| 2004/0049836 A1 | 3/2004 | Ashraf et al. |
| 2004/0123938 A1 | 7/2004 | Neculescu et al. |
| 2004/0162538 A1 | 8/2004 | Mueller et al. |
| 2004/0222553 A1 | 11/2004 | Desai et al. |
| 2006/0083900 A1 | 4/2006 | Ashraf |

FOREIGN PATENT DOCUMENTS

| | | | |
|---|---|---|---|
| WO | WO-01/87588 A2 * | 11/2001 | |
| WO | WO-01/88245 A2 * | 11/2001 | |
| WO | WO 03/039420 A | 5/2003 | |
| WO | WO 03/039421 A | 5/2003 | |
| WO | WO 2004/098475 A | 11/2004 | |

OTHER PUBLICATIONS

U.S. Appl. No. 60/557,272, filed Mar. 29, 2004, Fred Desai.
U.S. Appl. No. 10/966,759, filed Oct. 15, 2004, Arman Ashraf.
International Search Report for PCT/US2005/037282 mailed Feb. 24, 2006.

* cited by examiner

METHOD FOR PRODUCING A CORRUGATED STRETCH LAMINATE WITH A FREE FORMED PRINTED ELASTIC MEMBER

FIELD OF THE INVENTION

This invention relates to a method of forming a corrugated stretch laminate through the use of a free-formed printed elastomer that is elongated and joined to a substrate.

BACKGROUND

Disposable absorbent products like diapers typically include stretchable materials in the waist, cuff, and other regions to provide a snug fit and a good seal of the article. Pant-type absorbent articles may further include stretchable materials in the side portions for easy application and removal of the article and for sustained fit of the article. Stretchable materials have also been used in the ear portions for adjustable fit of the article. The stretchable materials utilized in these article regions may include elastomeric materials such as films, nonwovens, strands, scrims, and the like. In most cases, these designs deliver uniform and unidirectional stretch, most often in the lateral direction of the article. However, elastomeric materials are relatively expensive so their use in stretchable materials is desirably optimized. Additionally, if elastomeric materials are used without some type of cover material, the elastomeric materials may tend to exhibit increased drag on skin surface, which may result in discomfort to the wearer of the product.

Stretchable materials may be made in the form of a stretch laminate, which involves one or more elastomeric materials laminated to one or more layers of another material. While the laminate may improve wearer comfort, the laminate may exhibit more limited stretchability and/or considerable resistance to stretch. Several approaches exist addressing this resistance to stretch.

One approach for creating stretch laminates is by a stretch bonding method. Stretch bonded laminates are made by stretching an elastic in a first direction, bonding the stretched elastic to one or more materials such as a nonwoven, and releasing the tension from the elastic so that the materials gather. The resulting laminate typically will be extensible in the same direction in which the elastic was stretched. The gathered nonwoven tends to have a corrugated feel and increased caliper that can improve wearer comfort when such stretch bonded laminates are used in absorbent products. The gathered nonwoven may also exhibit improved opacity; a feature that may be desirable since improved opacity often suggests a high quality product.

The elastic may be supplied to the stretch bonding process (e.g., elastic strands purchased from a supplier) or formed in-situ within the process. Having the elastomeric material supplied to the process is not without problems. A problem with supplying elastomeric materials to the process is that processing flexibility is reduced. Any modification to the elastomeric material requires sufficient lead time so that the required elastomeric materials may be ordered, formulated, produced, shipped, and integrated. Having elastomeric material formation as an in-situ or in-line element to the stretch bonding process may address some of the supply problems; however, current in-process elastomeric material formation methods present a variety of processing difficulties.

A common problem with in-process formation of stretch laminates involves the structure and form of the elastomeric material. Typical elastomeric material formation involves extrusion of a molten elastomeric composition through an apertured die. The extrusion process limits the available compositions that may be extruded and the shapes and/or structures that may be extruded. The shape of the resulting elastomeric material may be dictated by the shape of the aperture within the die. Since the aperture is a fixed shape and dimension, the resulting elastic materials drawn through the aperture will typically be of a fixed shaped and dimension (i.e., a circular aperture will yield an elastic strand having a circular cross-sectional shape throughout the length of the strand). Thus, structural variability in extruded elastomeric materials may be difficult to achieve.

Extrusion also limits processing flexibility as to the elastomeric compositions that may be used. The extrusion of an elastomeric composition results in several unique processing challenges. For example, extrusion may present problems with regard to surging or draw resonance of the elastomeric composition. Both of these problems may be addressed by adjusting the formulation of the elastomeric composition. However, such adjustments to the elastomeric composition may, in turn, limit the structural or functional properties (e.g., modulus, tensile strength, etc.) of the resultant elastomeric materials.

Another problem that is seen with in-line extrusion of an elastomeric composition involves the maximum line speed that may be achieved. Extrusion may often be the bottle-neck in the process line. The quantity of elastic materials available to be stretch bonded may be ultimately limited by the amount of elastomeric composition that can be drawn through an apertured die. This through-put is variable depending upon such properties as the formulation of the elastomeric composition and the size and shape of the apertures. However, any given extrusion process traditionally yields a maximum through-put. Limits on the through-put of elastomeric composition through the apertured die are translated into reduced quantity of elastomeric material per unit time which then results in a reduced quantity of stretch bonded laminate per unit time.

An alternate approach of creating stretchable materials is disclosed in copending U.S. application Ser. Nos. 10/288,095, 10/288,126, and 10/429,433. This approach involves hot melt application of one or more thermoplastic elastomers onto a substrate (e.g., nonwoven), followed by incremental stretching of the substrate that confers the stretch properties of the elastomer to the substrate in a somewhat magnified form. This method allows for the deposition of any amount of an elastomer in any shape and direction, thus giving a wide variety of design flexibility which ultimately results in improved fit of the overall diaper product. However, the hot melt application method can be improved. Incremental stretching can physically break the fiber to fiber network within a nonwoven. As a result, an incrementally stretched nonwoven may appear shredded and be aesthetically undesirable. The shredded appearance can be avoided by using a nonwoven with a sufficiently high basis weight, but with increased basis weight comes increased cost. Furthermore, it is difficult for the hot melt application method to yield a stretch laminate that exhibits a gathered appearance as found in stretch-bonded laminates. Without a gathered nonwoven, the benefits of corrugated feel and increased caliper are missing. Furthermore, the opacity of stretch laminates resulting from the hot melt method can exhibit reduced opacity as compared to a like stretch bonded laminate (i.e., the stretch bonded laminate and hot melt laminate having nonwovens of like construction and basis weight).

In view of the above, it would be desirable to provide a cost effective stretch laminate comprising elastomeric materials that may be produced in-process without one or more of the aforementioned problems. It would be desirable to use such stretch laminates within specific areas of absorbent articles such as diapers and the like to provide a desired in-use benefit (e.g., sealing, containing, gasketing, body-conforming) for the article. It would also be desirable to provide an efficient and cost-effective process for producing the stretch laminates. Further, it would be desirable to provide a process for producing stretch laminates that do not require the use of externally supplied elastic members or in-process extrusion formed elastic members.

SUMMARY OF THE INVENTION

The present invention relates to a process for making a corrugated stretch laminate comprising the steps of delivering a first elastomeric composition to a print device to form an elastic member; removing the elastic member from the print device; joining the elastic member to a first substrate; and allowing the elastic member to recovery to form said corrugated stretch laminate.

In certain embodiments, the process may further comprise the steps of delivering a second elastomeric composition to a second print device; removing the second elastic member from the print device; elongating the second elastic member in a second direction; and joining the second elastic member to the first substrate. The first elastic member and the second elastic member may differ in a property selected from the group consisting of elasticity, melt viscosity, shape, pattern, add-on level, formulation, and combinations thereof.

In certain embodiments, the process may further comprise the steps of joining the elastic member to more than one substrate.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings.

DETAILED DESCRIPTION

The term "disposable" as used herein refers to products which generally are not intended to be laundered or otherwise restored or extensively reused in their original function, i.e., products that are intended to be discarded after a single use or a small number of uses. It is preferred that such disposable articles be recycled, composted or otherwise disposed of in an environmentally compatible manner.

The term "disposable absorbent article" as used herein refers to a device that normally absorbs and retains fluids. In certain instances, the phrase refers to devices that are placed against or in proximity to the body of the wearer to absorb and contain the excreta and/or exudates discharged from the body, and includes such personal care articles as fastened diapers, pull-on diapers, refastenable/prefastened diapers and pants, training pants, swim diapers, adult incontinence articles, feminine hygiene articles, and the like. In other instances, the term also refers to protective or hygiene articles, for example, bibs, wipes, bandages, wraps, wound dressings, surgical drapes, and the like.

The term "fibrous substrate" as used herein refers to a material comprised of a multiplicity of fibers that could be either a natural or synthetic material or any combination thereof, for example, nonwoven webs, woven webs, knitted fabrics, and any combinations thereof.

The term "substrate" as used herein refers to a material that includes either a natural or synthetic material or any combination thereof, for example, nonwoven webs, woven webs, knitted fabrics, films, film laminates, nonwoven laminates, sponges, foams, and any combinations thereof.

The term "nonwoven" as used herein refers to a material made from continuous and/or discontinuous fibers, without weaving or knitting, by processes including, but not limited to, spun-bonding, carding and melt-blowing. The nonwoven webs can comprise one or more nonwoven layers, wherein each layer can include continuous and/or discontinuous fibers. Nonwoven webs can also comprise bicomponent fibers, which can have core/shell, side-by-side, or other known fiber structures.

The term "elastic" or "elastomeric" as used herein refers to any material that upon application of a biasing force, can stretch to an elongated length of at least about 160 percent of its relaxed, original length, without rupture or breakage, and upon release of the applied force, recovers at least about 55% of its elongation. The material desirably may recover substantially to its original length. That is, the recovered length may be less than about 120 percent, may be less than about 110 percent, or may be less than about 105 percent of the relaxed original length.

The term "inelastic" refers herein to any material that does not fall within the definition of "elastic" above.

The term "elastomer" as used herein refers to a polymer exhibiting elastic properties.

The term "extensible" or "inelastically elongatable" refers herein to any material that upon application of a biasing force to stretch beyond about 110 percent of its relaxed original length will exhibit permanent deformation, including elongation, rupture, breakage, and other defects in its structure, and/or changes in its tensile properties.

The term "machine direction" (alternatively referred to herein as "MD") is a well known term of art that is generally understood to refer to the direction corresponding to the length of a web as it is formed or processed. The machine direction typically corresponds to the path the web travels during formation or processing.

The term "cross-machine direction" (alternatively referred to herein as "CD") refers to the direction which is 90° to the machine direction.

The term "free-formed" refers herein to an elastic member formed by printing of an elastomeric composition in absence of a substrate. The resulting "free-formed" elastic member may be conveyed and processed without the need for a substrate. As is described below, a carrier substrate may be used in limited instances of the process such as during start-up; however, any elastic member formed by printing of the elastomeric composition to the carrier substrate may be discarded and is not typically used to form the resultant corrugated stretch laminate of the present invention.

Figure 1:
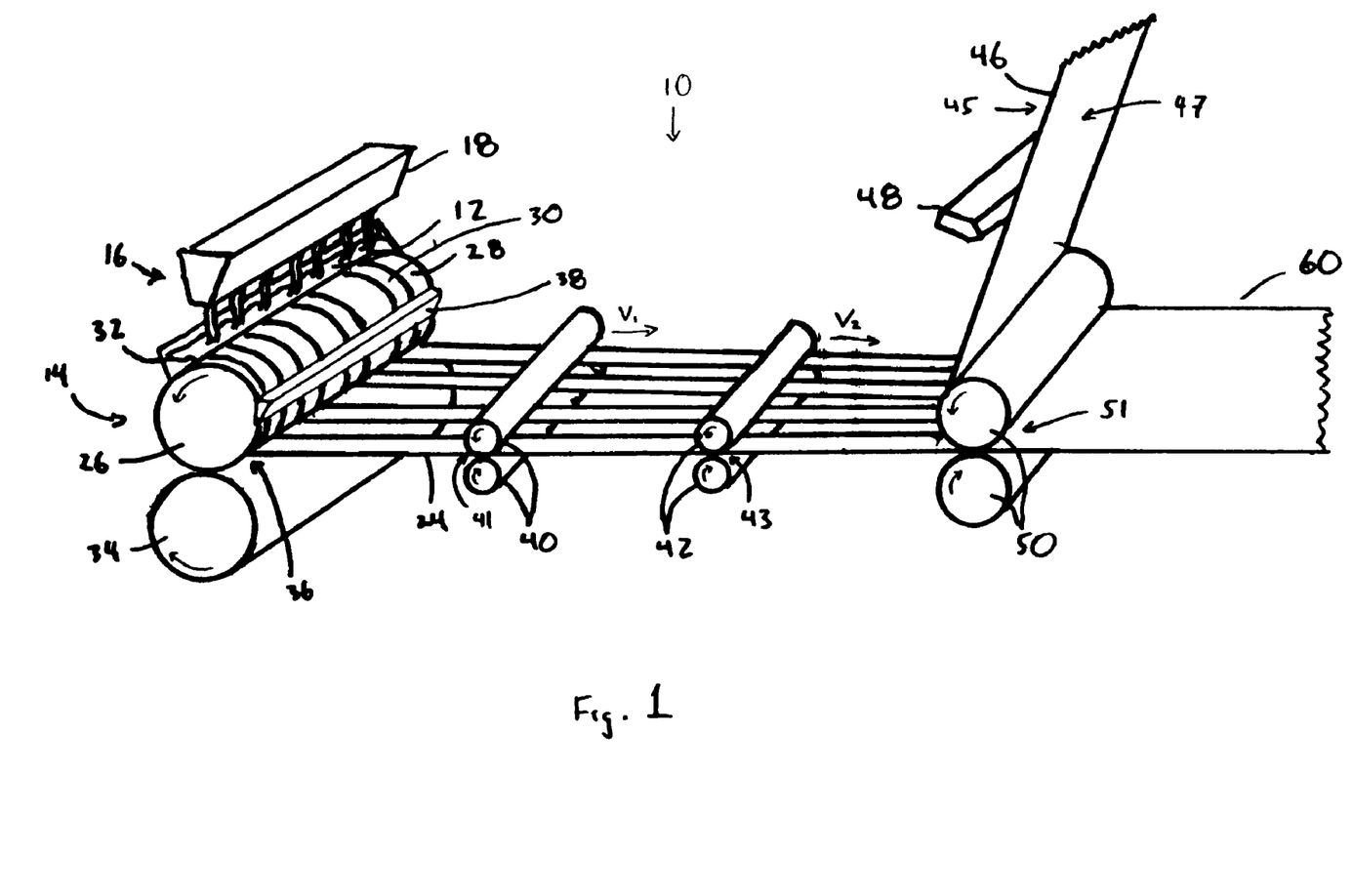
FIG. 1 is a schematic illustration of a representative process of the present invention.

One process of the present invention, as illustrated in FIG. 1, relates to a process 10 of manufacturing a corrugated stretch laminate that includes a free-formed printed elastic member including the steps of delivering a first elastomeric composition onto a print device; removing the first elastomeric composition from the print device in the form of an elastic member; elongating the elastic member in a first direction; and joining the elastic member to a first substrate to form said corrugated stretch laminate.

Delivering A First Elastomeric Composition

Delivery of a first elastomeric composition 12 to a print device 14 may be performed according to a variety of methods and by a variety of devices. The delivery mechanism 16 is any device that supplies an amount of elastomeric composition 12 to the print device 14. Suitable delivery mechanisms 16 include, for example, devices such as slot coaters, curtain coater, baths, sprayers, or extruders. As illustrated in FIG. 1, the delivery mechanism 16 may involve a slot coater 18 delivering the elastomeric composition 12 to the print device 14. The slot coater 18 may be provided in proximity to the exterior surface of the print device 14. The slot coater 18 or other delivery mechanism 16 may also serve to heat, mix, consolidate, transport, and/or process the elastomeric composition 12. The slot coater 18 may dispense the elastomeric composition 12 through a plurality of apertures. The apertures should be sized to provide an effective amount of elastomeric composition 12 to the print device 14 so that the print device 14 may form an elastic member 24. The slot coater 18 may meter delivery such that a defined amount of elastomeric composition 12 is delivered to the print device 14 per unit time.

A variety of print techniques and devices are well-known in the art and may be used in the present invention. For example, suitable print devices 14 include print rolls, print webs, gravure rolls, gravure webs, print screens, lithographic rolls, relief rolls, reverse rolls, knife-over roll, notched knife-over roll, offset derivations thereof, and combinations thereof.

As shown in FIG. 1, the print device 14 may be a gravure printing roll 26 or gravure printing belt. When a gravure roll 26 is employed, as shown in FIG. 1, the gravure roll 26 may have an exterior surface 28 interspersed with one or more cells (or grooves) 30. The gravure roll 26 may exhibit rotation about an axis that runs parallel to the cross-machine direction. The cells or grooves 30 are indentations on the exterior surface 28 of the gravure roll 26 that permit receipt of a liquid material (e.g., the elastomeric composition 12) that is intended for transfer from the gravure roll 26 to form the elastic member 24. Since temperature can affect the viscosity and, consequently, the processing character of the elastomeric composition 12, it may be desirable that the roll 26 is capable of being heated and/or cooled so that the process can run at a commercially-reasonable speed.

The elastomeric composition 12 may flow onto the exterior surface 28 of the gravure roll 26 and into the cells 30. A doctor blade 32 may be provided to wipe the exterior surface 28 of the gravure roll 26 substantially free of any residual elastomeric composition 12. The doctor blade 32 is also useful in providing for uniform distribution of the elastomeric composition 12 into the cells 30. In certain embodiments, more elastomeric composition may be present on the exterior surface 28 of the gravure roll 26 than is required to fill the cells 30 given a prescribed processing speed. In such cases, the doctor blade 32 may also serve as a dam causing a reservoir of elastomeric composition 12 to build behind the doctor blade 32. This damming effect may compensate for delivery rate variations of the delivery mechanism 16. In some embodiments, the doctor blade 32 may be an integral element of the print device 14.

The elastomeric composition 12 may be applied to the print device 14 in a fluid, fluid-like, or molten state. In some embodiments, the elastomeric composition 12 may be heated to achieve the fluid, fluid-like, or molten state. Heating of the elastomeric composition 12 may be performed by the delivery mechanism 16, the print device 14, or some other device capable of heating the elastomeric composition 12. As the gravure roll 26 rotates, the elastomeric composition 12 may cool and may become less fluid or molten. To assist in this cooling, the gravure roll 26 may be temperature controlled. As the gravure roll 26 rotates and cools the elastomeric composition 12, the elastomeric composition 12 may increase in viscosity thus improving releasability from the gravure roll 26. Other cooling means known in the art may also be used in addition to or instead of a chilled gravure roll 26. Further discussion of the interaction between a molten, fluid, and/or fluid-like elastomeric composition 12 and a relatively cooler roll is discussed in U.S. application Ser. No. 60/557,272 filed on Mar. 29, 2004.

The relative dimensions of the resulting elastic member 24 may be varied to impart specific stretch characteristics or geometries to the resultant corrugated stretch laminate 60. The relative size, shape, and orientation of the elastic members 24 may be altered by altering certain parameters and/or configurations of the print device 14. In the case of a gravure roll 26, the gravure cell 30 size, shape, and orientation may be altered to affect the relative size, shape, and orientation of the elastic members 24. Likewise, the formulation of the elastomeric composition 12 may be altered to affect the relative size, shape, and orientation of the elastic members 24. For example, the basis weight of an elastic member 24 may be altered by utilizing a gravure roll 26 having cells 30 of variable volume. By way of further example, the pattern and location of the cells 30 on the gravure roll 26 impacts the shape of the resulting elastic members 24. This allows for the formation of elastic members 24 of numerous forms and shapes, such as, for example, a film, an apertured film, a strand, a ribbon, and the like.

The stretch and recovery property of the elastic member 24 can be varied discretely (i.e., the property changes in a stepwise manner) or continuously. An example of such stepwise change would be to apply more elastomeric composition 12 in certain portions of the elastic member 24 where stretch requirements are high while applying less elastomeric composition 12 to other portions where the stretch requirements are less demanding. The stretch and recovery property can also be varied continuously, either linearly or non-linearly. Continuous changes in stretch property may be achieved by the cell 30 pattern design. For example, a cell 30 pattern designed in such a way that the cell 30 depth decreases gradually along the length of the cell 30, thus resulting in a printed pattern where the amount of deposited elastomeric composition 12 decreases continuously from one end of the elastic member 24 to the other.

The gravure roll 26 may be paired with an optional transfer roll 34. The transfer roll 34 rotates on an axis parallel to the axis of rotation for the gravure roll 26. The transfer roll 34 may be made from or coated with a relatively pliant material such as silicone rubber having a hardness of 55 Shore A. The transfer roll 34 may be comprised of and/or coated with a material having an increased surface energy than that of the gravure roll 26 such that the elastomeric composition 12 exhibits preferential adhesion to the transfer roll 32. It may be desirable that the transfer roll 34 is capable of being heated and/or cooled. The gravure roll 26 and transfer roll 34 meet at the nip point 36. The temperature and pressure applied at the nip point 36 by the gravure roll 26 and transfer roll 34 may be controlled to improve the releasability of the elastomeric composition 12 in the form of an elastic member 24.

In suitable alterative embodiments, the print device 14 may be an indirect print device (also known as offset printing). Indirect application involves printing the elastomeric composition 12 to an intermediate surface prior to removal of the elastic member 24. For example, off-gravure printing may involve the cells 20 of the gravure roll 26 applying the elastomeric composition 12 to an intermediate surface (e.g., an intermediate roll or web) which may have good thermal stability. The intermediate surface may then convey the elastomeric composition 12 to a point where the elastomeric composition 12 may be removed as the elastic member 24. The indirect print device allows for a wider range of operating temperatures because the fluid or molten elastomeric composition 12; in particular, use of an indirect print method allows additional time for the elastomeric composition 12 to cool thereby forming the elastic member. In particular, it is believed that the indirect print device is particularly suitable for elastomeric compositions 12 that require heating to unusually high temperatures before fluid or molten character is exhibited. While in some embodiments the elastomeric composition 12 will retain some fluid or molten character at the point of transfer from the print roll (e.g., gravure roll 26) to the intermediate surface, it is anticipated that the elastomeric composition 12 may be substantially cooled and/or solidified so as to form the elastic member 24 at the point of transfer from the print roll (e.g., gravure roll 26) to the intermediate surface.

Removing the Elastic Member

The elastic member 24 may be released from the gravure roll 26 or any other print device by gravity and/or by a force applied in the process. For example, the elastic member 24 may be drawn from the gravure roll 26 by the adhesive force applied by the back-up roll 34. Further, the elastic member 24 may be drawn from the gravure roll 26 by machine direction forces applied by downstream process steps. In such an example, a conveying device (such as drive rolls, off-speed rolls, or any other powered device that transports or applies a force to the elastic member 24) may be positioned downstream of the print device 14 and may exert a force to the elastic member 24. At least a portion of the force exerted by the conveying device may be exerted on the elastic member 24 to aid in removal of the elastic member 24 from the print device 14.

In certain embodiments, the elastic member 24 may be released from the print device 14 by use of a doctor or creping blade. The use of doctor blades and creping blades are well known is the art and may be selected for the given print device 14 used in the present invention. In other embodiments, the elastic member 24 may be released from the print device 14 by use of an air knife 38. Other means for removing a substrate from a process roll are known in the art and may be used.

The elastic member 24 is shown in FIG. 1 as being conveyed without support (i.e., the elastic member 24 has sufficient tensile strength and abrasion resistance to be conveyed on it own). In other suitable embodiments, the elastic member 24 may be conveyed by any web conveying device such as a belt or series of rolls.

It should be noted that a carrier substrate such as, but not limited to, a nonwoven web may be necessary for the efficient start-up of the processes described herein. Such a carrier substrate is used as a support mechanism to facilitate conveyance of the elastic member 24 through the process. An effective machine direction length of the carrier substrate may be used; an effective length being the length necessary to convey the elastic member 24 through the process so that the elastic member 24 can then be free-formed (i.e., elastic member being formed without the need for a carrier substrate).

Elongating the Elastic Member

Referring to FIG. 1, the elastic member 24 may be subjected to tensioning in a first direction, which results in elongation of the elastic member 24. The elastic member 24 may be elongated up to the point of catastrophic failure; however, the elastic members 24 is ideally elongated an effective amount such when laminated with another material the resultant stretch laminate 60 exhibits at least some degree of corrugation. In certain embodiments, the elastic member 24 is elongated from at least about 50% to about 150%. In other embodiments, the elastic member 24 is elongated at least about 150% to about 250%. However, elongation in excess of 250% and less than 50% may also be performed.

Elongation of the elastic member 24 may be performed by means well known in the art. For example, elongation in the machine direction can be accomplished by conveying the elastic member 24 through off-speed rolls. As the name implies, off-speed rolls involve a sequence of rolls driven at variable speeds. FIG. 1 illustrates a first set of off-speed rolls 40 and a second set of off-speed rolls 42. The first off-speed rolls 40 form a first nip 41 which imparts a first velocity $V_1$ to the elastic member 24 as the elastic member 24 passes the first nip 41. The second off-speed rolls 42 form a second nip 43 which imparts a second velocity $V_2$ to the elastic member 24 as the elastic member 24 passes the second nip 43. When the second velocity $V_2$ is greater to the first velocity $V_1$, tension may be imparted to the elastic member 24. The tension preferably elongates the elastic member 24 in the machine direction. Clearly, to maintain the machine direction elongation, the elastic member 24 must maintain the second velocity $V_2$ until joined with a substrate as provided for below. In other suitable embodiments, the number of off-speed rolls 40, 42 may vary and may be omitted altogether. If the off-speed rolls 40, 42 are to be omitted, machine direction elongation may be achieved by imparting the first velocity $V_1$ and second velocity $V_2$ with existing process components. For example, the first velocity $V_1$ may be imparted by the rotational speed of the gravure roll 24 and transfer roll 34 during the formation of the elastic member 24. The second velocity $V_2$ may be imparted by bonding rolls 50 for use in joining a substrate 46 to the elastic member 24 as provided for below. The increase in velocity results in tensioning and elongation of the elastic member 24 between the formation of the elastic member 24 and the joining of the substrate 46. In other embodiments, the gravure roll 24; the off-speed rolls 40, 42; the bonding rolls 50; and any other process roll may impart a varying velocity to the elastic member 24. A gradually increasing viscosity may be desirable to prevent catastrophic rupture of the elastic member 24 which may occur with a sudden increase in velocity.

Elongation of the elastic member 24 in the cross machine direction can be accomplished by subjecting the elastic member 24 to "Mount Hope" rolls, tentering frames, angled idlers, angled nips, slatted spread rollers, edge pull web stretchers, and the like, each of which is known to those skilled in the art. For example, cross machine direction elongation may be achieved through the use of one or more edge pull rollers. The edge pull rollers form a nip point through which the elastic member 24 may be fed. The edge pull rollers may be canted outwardly from the machine direction path of travel of the elastic member 24. The canting creates a cross-machine direction vector of force that strains and elongates the elastic member 24. The angle of canting off from the machine direction may be varied to impart cross-machine direction force vectors of varying magnitude. The use of a series of edge pull rollers may be preferred to achieve the requisite elongation of the elastic member 24. Furthermore, a series of edge pull rollers may allow for a graduated elongation of the elastic member so as to prevent imposition of violent web strain and potential failure of elastic member. Further discussion of cross-machine direction elongation may be found in U.S. patent application Ser. No. 10/966,759 filed on Oct. 15, 2004 in the name of Arman Ashraf.

Elongation of the elastic member 24 in directions other than the cross-machine direction and machine direction within the plane of the elastic member 24 may be performed by combining machine direction elongation techniques and cross-machine direction elongation techniques. Such combination of machine direction elongation force and cross-machine direction elongation force may yield an effective force vector sum. In some instances, the force vector may be in a direction other than the machine direction or cross-machine direction. The corrugated stretch laminate 60 that results may exhibit biaxial stretch and recovery, which is the ability to stretch and recover in two orthogonal directions.

Joining a Substrate

The elastic member 24 is joined to a first substrate 46. The first substrate 46 may be provided in a substantially continuous manner (i.e., web is supplied continuously during the normal operation of the process) such as from a bulk supply roll. The first substrate 46 may have a first surface 45 and second surface 47. Suitable first substrates 46 may include films, knitted fabrics, woven fibrous webs, nonwoven fibrous webs, laminates, or combinations thereof. In certain embodiments, the first substrate 46 is a fibrous substrate such as an extensible nonwoven web that comprises polyolefin fibers and/or filaments. The first substrate 46 may also be a laminate comprising a fibrous substrate such as a nonwoven-film laminate, which for example, may be used as the outercover of a disposable diaper, training pant, adult incontinence product, etc. In other embodiments, the first substrate 46 may be provided by on-line formation. In such an embodiment, the process 10 may be equipped with a formation station where the first substrate 46 is created. Methods for creating a first substrate 46 such as, for example, films, knitted fabric, woven fibrous webs, nonwoven fibrous webs, laminates, or combinations thereof are well known in the art. For example, the first substrate 46 may comprise a nonwoven web comprising spunbonded filaments; a spunbond extrusion station may be utilized to provide the first substrate 46.

The first substrate 46 and the elastic member 24 may be bonded to one another. Generally, the elastic member 24 may be bonded to one surface of the first substrate 46. Bonding of the first substrate 46 and the elongated elastic member 24 may be conducted by a variety of bonding methods well known in the art such as adhesive, thermal, mechanical, ultrasonic bonding. Bonding may be relatively continuous or intermittent. Relatively continuous bonding implies that the first substrate 46 and the elastic member 24 are bonded together over substantially all of one or more dimensions of a common interface between the first substrate 46 and the elastic member 24. Intermittent bonding implies that the first substrate 46 and the elastic member 24 are bonded together with one or more individual, discrete bonds that are not continuous or bond patterns having open areas free of bonds. As illustrated in FIG. 1, bonding may be performed by use of a first adhesive applicator 48. The adhesive applicator 48 applies an effective amount of adhesive so as to join the first substrate 46 and the elastic member 24. Adhesive may be applied to the first substrate 46, the elastic member 24, or to both.

Figure 2:
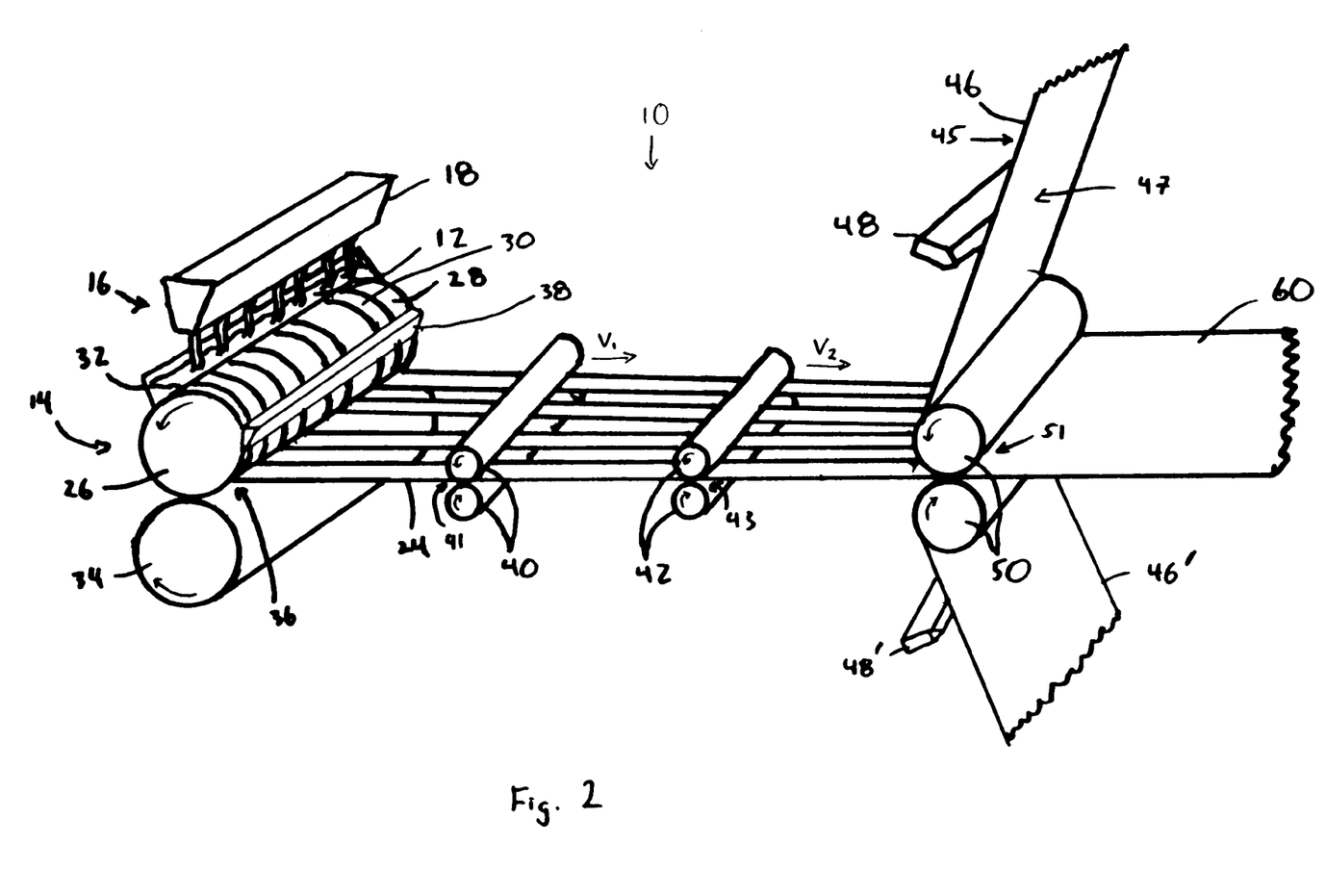
FIG. 2 is a schematic illustration of another representative process of the present invention.

The first substrate 46 and the elastic member 24 may be brought together in a face-to-face relationship by way of the bonding rolls 50. The bonding rolls 50 may form a bonding nip 51 whereby the first substrate 46 and elastic member 24 are brought into contact and may be compressed. Compression may improve adhesive spread and/or penetration into the elastic member 24 and/or the substrate 46 thus providing for a stronger adhesive bond. In the case of thermo-mechanical bonding, the bonding rolls 50 may impart bonding by heat and/or pressure so as to fuse the substrate 46 and elastic member 24. In certain embodiments, the elastic member 24 may exhibit sufficient residual adhesive character so that an adhesive is unnecessary; however, even if the elastic member 24 exhibits sufficient residual adhesive character, an adhesive may still be used In other suitable embodiments, more than one substrate may be joined to the elastic member 24. The substrates 46 may include films, knitted fabrics, woven fibrous webs, nonwoven fibrous webs, laminates, or combinations thereof. In certain embodiments, the substrate 46 is a fibrous substrate such as an extensible nonwoven web that comprises polyolefin fibers and/or filaments. The substrate 46 may also be a laminate comprising a fibrous substrate such as a nonwoven-film laminate, which for example, may be used as the outercover of a disposable diaper, training pant, adult incontinence product, etc. In other embodiments, the substrate 46 may be provided by on-line formation. For example, the process of the present invention may be equipped with a formation station where the substrate 46 is created. Methods for creating a first substrate 46 such as, for example, films, knitted fabric, woven fibrous webs, nonwoven fibrous webs, laminates, or combinations thereof are well known in the art. The relative positioning of the substrates with the elastic member 24 are numerous. Bonding of multiple substrates (see FIG. 2) and the elastic member 24 may be conducted by a variety of bonding methods well known in the art such as adhesive, thermal, mechanical, ultrasonic bonding. Bonding may be relatively continuous or intermittent. In certain embodiments, the elastic member 24 may exhibit sufficient residual adhesive character so that an adhesive is unnecessary; however, even if the elastic member 24 exhibits sufficient residual adhesive character, an adhesive may still be used An example of a process incorporating multiple substrates is shown in FIG. 2. FIG. 2 is similar with respect to the process shown in FIG. 1. A first substrate 46 and a second substrate 46' may be joined in a face-to-face relationship with the elastic member 24 therebetween. A second adhesive applicator 48' may be used to apply an effective amount of adhesive so as to join the second substrate 46' and the elastic member 24. Adhesive may be applied to the first substrate 46, second substrate 46', the elastic member 24, or to combinations thereof.

Referring to FIGS. 1 and 2, a corrugated stretch laminate 60 results upon removal of the elongating tension is from the elastic member 24. The corrugated stretch laminate 60 resulting from the process 10 exhibits stretch and recovery in at least the one direction. Stretch and recovery may be exhibited in the cross-machine direction, machine direction, and/or in some other resultant direction. The elastic member 24 or the resulting corrugated stretch laminate 60 may be subjected to additional treatments such as cooling, pressing (e.g., passing between a pair of nip rolls), crosslinking, curing (e.g., via chemical, thermal, radiation methods), heating, ring-rolling, and combinations thereof, to enhance the elastic and mechanical properties of the laminate 60.

Figure 3A:
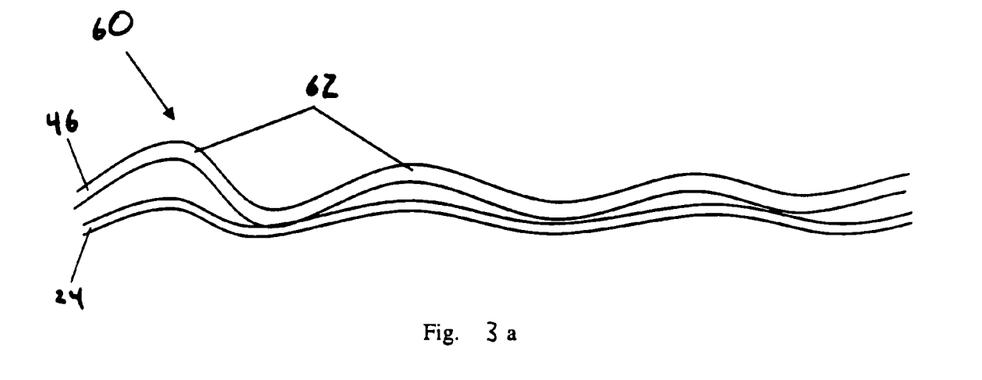
FIG. 3a is an enlarged cross-sectional view of a corrugated stretch laminate in a relaxed state wherein tension has been released from the elastic members.
Figure 3B:
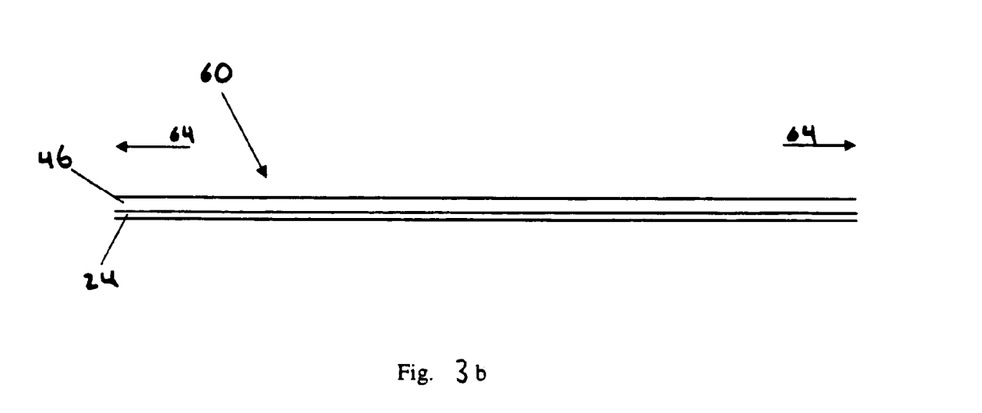
FIG. 3b is an enlarged cross-sectional view of the corrugated stretch laminate of FIG. 3a with a tensioning force applied thereto.

A corrugated stretch laminate 60, as shown in FIGS. 3a and 3b, results from the apparatus and method as described above. FIG. 3a is an enlarged sectional view along the machine direction of the corrugated stretch laminate 60 in a recovered state wherein tension has been released from the elastic member 24. The first substrate 46 may gather and foreshorten so as to produce a plurality of corrugations 62 in the resultant corrugated stretch laminate 60. Corrugations 62 are the irregular hills and valleys that alternate in the corrugated stretch laminate 60.

Once a tensioning force 64 is placed on the corrugated stretch laminate 60, the corrugations 62 may enable the substrate 46 to extend with the elastic member 24 at least to the point of reaching a force wall, which is about where the corrugations 62 flatten out and the substrate 46 requires significant force to elongate further, as shown in FIG. 3b. As the strain is removed, the elastic member 24 may recover and contract back toward its original, relaxed length. This contraction re-establishes the corrugations 62 of the corrugated stretch laminate 60.

Figure 4:
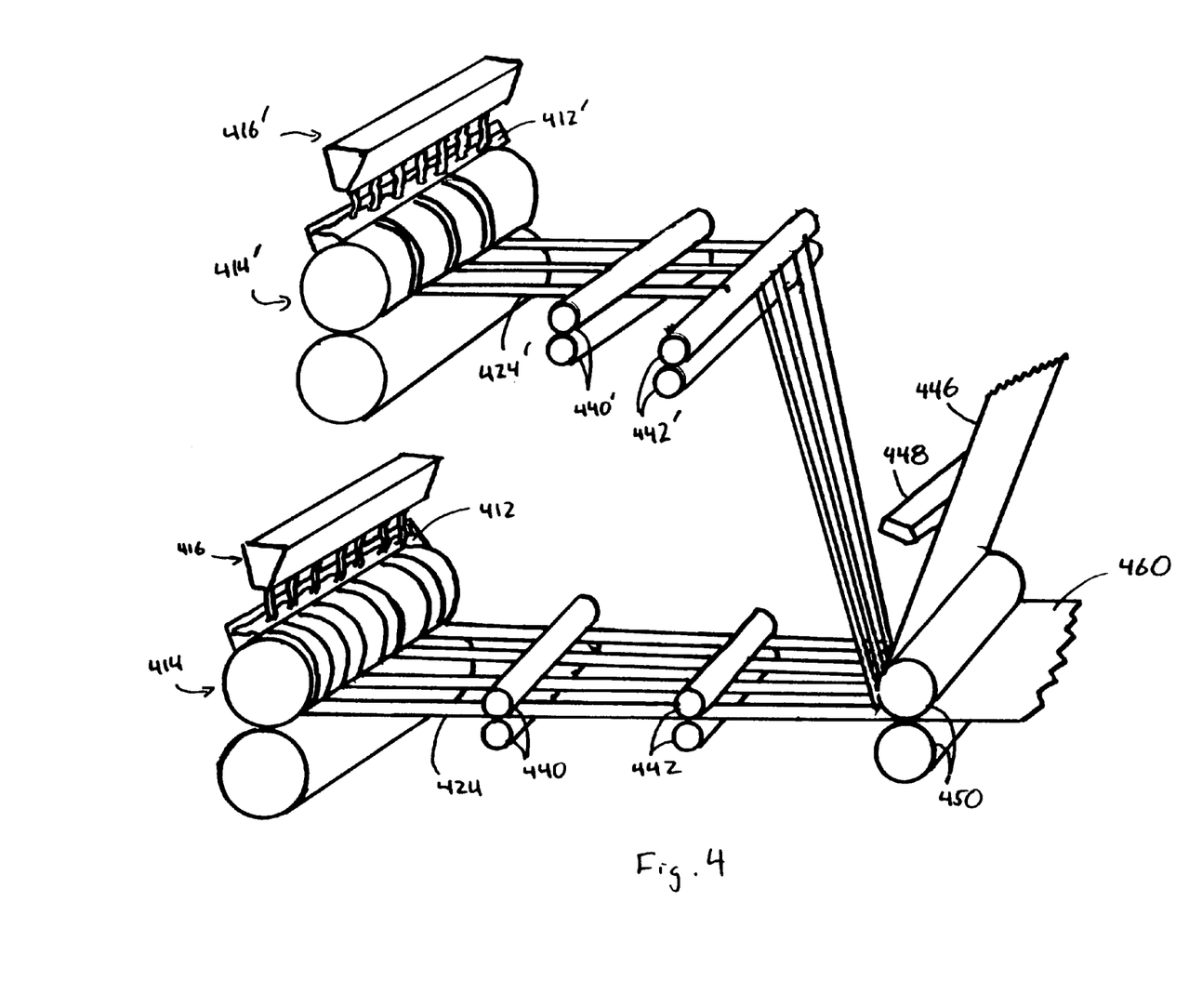
FIG. 4 is a schematic illustration of another representative process of the present invention.

In another embodiment of the present invention for manufacturing a corrugated stretch laminate that includes a free-formed printed elastic member, multiple print devices may be used to apply the same or different elastomeric compositions in order to form elastic members. In one suitable embodiment as shown in FIG. 4, a corrugated stretch laminate 460 may be formed by use of two print devices 414, 414' forming elastic members 424, 424'.

A first elastomeric composition 412 may be delivered by a first delivery mechanism 416 to a first print device 414. The first delivery mechanism 416 is any device that supplies an amount of first elastomeric composition 412 to the first print device 414 and includes those delivery mechanisms previously discussed. A variety of print techniques and devices, which are well-known in the art as previously discussed, may be used in the present embodiment. The first elastic member 424 may be released from the print device 414 by gravity, a force applied in the process, a creping blade, an air knife, or other means known in the art.

A second elastomeric composition 412' may be delivered by a second delivery mechanism 416' to a second print device 414'. The second delivery mechanism 416' is any device that supplies an amount of second elastomeric composition 412' to the second print device 414' and includes those delivery mechanisms previously discussed. A variety of print techniques and devices, which are well-known in the art as previously discussed, and may be used in the present embodiment. The second elastic member 424' may be released from the print device 414' by gravity, a force applied in the process, a creping blade, an air knife, or other means known in the art.

The first and second elastomeric composition 412, 412' may be of the same or of differing formulations, shape, or form. In some embodiments, the first and second elastic members 424, 424' may differ in a property such as elasticity, melt viscosity, shape, pattern, add-on level, and combinations thereof.

The first and second elastic members 424, 424' may be subjected to tensioning, which results in elongation of the first and second elastic member 424, 424'. The first and second elastic members 424, 424' may be elongated up to the point of catastrophic failure; however, the first and second elastic members 424, 424' are typically elongated an effective amount such that the resultant corrugated stretch laminate 460 exhibits at least some degree of corrugation. The first and second elastic members 424, 424' may be tensioned using the same or different tensioning techniques. In certain embodiments, the first and second elastic members 424, 424' are elongated from at least about 50% to about 150%. In other embodiments, the elastic member 424 is elongated at least about 150% to about 250%. However, elongation in excess of 250% and less than 50% may also be performed. The first and second elastic members may have the same or different degrees of elongation. Methods for tensioning and elongating process webs are well known in the art and have been described previously. FIG. 4 shows the first elastic member 424 being elongated by a set of off-speed rolls 440, 442 and the second elastic member 424' being elongated by a separated set of off-speed rolls 440', 442'. While FIG. 4 shows the first and second elastic member 424, 424' being elongated by separate elongation apparatus (e.g., off-speed rolls), in certain embodiments, the first and second elastic members 424, 424' may elongated by a single elongation apparatus (e.g., the first and second elastic members 424, 424' may be conveyed together through a set of off-speed rolls).

A first substrate 446 may be provided in a substantially continuous manner (i.e., web is supplied continuously during the normal operation of the process). Suitable first substrates 446 have been discussed previously and may include films, knitted fabric, woven fibrous webs, nonwoven fibrous webs, laminates, or combinations thereof. The first substrate 446 and the elastic member 424 may be bonded to one another. Intermittent and/or continuous bonding of the first substrate 446 and the elastic members may be conducted by a variety of bonding methods well known in the art such as adhesive, thermal, mechanical, ultrasonic bonding. In some embodiments as shown in FIG. 4, bonding may be performed by use of an adhesive delivered by an adhesive applicator 448. The adhesive applicator 448 applies an effect amount of adhesive so as to prevent delamination of the first substrate 446 and the elastic member 424 during normal use conditions of the resultant corrugated stretch laminate 460. Adhesive may be applied to the first substrate 446, the elastic member 424, or to both. Bonding rolls 450 may be used form a bonding nip whereby the first substrate and elastic member are brought into contact and may be compressed. Compression may improve adhesive spread and/or penetration into the elastic member 424 and the substrate 446 thus providing for a stronger adhesive bond. In certain embodiments, the elastic member 424 may exhibit sufficient residual adhesive character so that an adhesive is unnecessary; however, even if the elastic member 424 exhibits sufficient residual adhesive character, an adhesive may still be used.

In certain embodiments, the first and second elastic members 424, 424' may be joined to the first substrate 446 in a variety of configurations. For example, the first and second elastic members 424, 424' may be discretely spaced such that the first and second elastic members 424, 424' do not overlap. By way of further example, the first and second elastic members 424, 424' may overlap or interrelate.

A corrugated stretch laminate 460 results from the bonding of the elastic members 424, 424' to the first substrate 446. The corrugated stretch laminate 460 resulting from the process shown in FIG. 4 exhibits stretch and recovery in at least the one direction. The elastic members 424, 424' or the resulting corrugated stretch laminate 460 may be subjected to additional treatments such as cooling, pressing (e.g., passing between a pair of nip rolls), crosslinking, curing (e.g., via chemical, thermal, radiation methods), heating, ring-rolling, and combinations thereof, to enhance the elastic and mechanical properties of the laminate 460.

Elastomeric Compositions

A variety of elastomeric compositions may be suitable for use in the present invention. Such suitable elastomeric compositions include thermoplastic elastomers that may be in the form of homopolymers (e.g., poly(isoprene)), block copolymers, random copolymers, alternating copolymers, and graft copolymers. The elastomeric composition may comprise from about 20% to about 100%, by weight, of the thermoplastic elastomer. Suitable thermoplastic elastomers may be selected from the group comprising polyvinylarenes, metallocene-catalyzed polyolefins, polyesters, polyurethanes, polyether amides, and combinations thereof. Preferred elastomeric compositions include vinylarene block copolymers. Block copolymers include variants such as diblock, triblock, tetrablock, or other multi-block copolymers having at least one vinylarene block. Exemplary vinylarene block copolymers include styrene-butadiene-styrene, styrene-isoprene-styrene, styrene-ethylene/butylene-styrene, styrene-ethylene/propylene-styrene, and the like. Commercially available styrenic block copolymers include KRATON® from the Shell Chemical Company of Houston, Tex.; SEPTON® from Kuraray America, Inc. of New York, N.Y.; and VECTOR® from Dexco Chemical Company of Houston, Tex. Commercially available metallocene-catalyzed polyolefins include EXXPOL® and EXACT® from Exxon Chemical Company of Baytown, Tex.; AFFINITY® and ENGAGE® from Dow Chemical Company of Midland, Mich. Commercially available polyurethanes include ESTANE® from Noveon, Inc., Cleveland, Ohio. Commercial available polyether amides include PEBAX® from Atofina Chemicals of Philadelphia, Pa. Commercially available polyesters include HYTREL® from E. I. DuPont de Nemours Co., of Wilmington, Del.

The elastomeric compositions may further comprise processing aids and/or processing oils. Such aids and/or oils may be used to adjust the melt viscosity of the compositions. They include conventional processing oils, such as mineral oil, as well as other petroleum-derived oils and waxes, such as paraffinic oil, naphthenic oil, petrolatum, microcrystalline wax, paraffin or isoparaffin wax. Synthetic waxes, such as Fischer-Tropsch wax; natural waxes, such as spermaceti, carnauba, ozokerite, beeswax, candelilla, ceresin, esparto, ouricuri, rezowax, and other known mined and mineral waxes, are also suitable for use herein. Olefinic or diene oligomers and low molecular weight resins may also be used herein. The oligomers may be polypropylenes, polybutylenes, hydrogenated isoprenes, hydrogenated butadienes, or the like, with a weight average molecular weight between about 350 and about 8000.

In one embodiment, a phase change solvent may be used as the processing aid. It can be incorporated into the elastomeric composition to lower the melt viscosity, rendering the composition processable at a temperature of 175° C. or lower, without substantially compromising the elastic and mechanical properties of the composition. Typically, the phase change solvent exhibits a phase change at temperatures ranging from about 40° C. to about 250° C. The phase change solvent has the general formula:

$R'\text{-}L_y\text{-}(Q\text{-}L_x)_{n-1}\text{-}Q\text{-}L_y\text{—}R;$  (I)

$R'\text{-}L_y\text{-}(Q\text{-}L_x)_n\text{—}R;$  (II)

$R'\text{-}(Q\text{-}L_x)_n\text{—}R;$  (III)

$R'\text{-}(Q\text{-}L_x)_{n-1}\text{-}Q\text{-}L_y\text{—}R;$  (IV)

$R'\text{-}(Q\text{-}L_x)_{n-1}\text{-}Q\text{-}R;$ or  (V)

a mixture thereof;

wherein Q may be a substituted or unsubstituted difunctional aromatic moiety; L is $CH_2$; R and R' are the same or different and are independently selected from H, CH3, COOH, $CONHR_1$, $CONR_1R_2$, $NHR_3$, $NR_3R_4$, hydroxy, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 1 to 7. Detailed disclosure of the phase change solvents can be found in U.S. Ser. application Ser. No. 10/429,432, filed on Jul. 2, 2003.

In addition the elastomeric composition can comprise stabilizers and the like. For example, stabilizers can include both antioxidants and light stabilizers. Suitable antioxidants include sterically hindered phenolics. A commercially available antioxidant suitable for use in the elastomeric compositions of the present invention is IRGANOX 1010 available from Ciba Specialty Chemicals North America of Tarrytown, N.Y. Suitable light stabilizers include hindered amine light stabilizers. A commercially available ultraviolet light stabilizer is TINUVIN 123 also available from Ciba Specialty Chemicals North America.

In certain embodiments, the elastomeric composition may also comprise a modifying resin. Modifying resins are particularly useful in elastomeric compositions where the thermoplastic elastomer is a block copolymer. Suitable modifying resins should preferably associate or phase mix with soft blocks of the thermoplastic elastomer. Modifying resins should have a sufficiently high average molecular weight. Suitable modifying resins include low molecular weight elastomers and/or elastomeric precursors of the above thermoplastic elastomers, and optional crosslinkers, or combinations thereof. Modifying resins useful herein include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; vinylarene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. "C5 hydrocarbon resins" and "C9 hydrocarbon resins" are disclosed in U.S. Pat. No. 6,310,154. The elastomeric composition may comprise from about 0% to about 60%, by weight, of the modifying resin.

In one certain embodiment, the elastomeric elastomer may be formulated as described in copending U.S. patent application Ser. No. 10/610,605, filed in the name of Ashraf, et al. on Jul. 1, 2003. The elastomeric composition comprises an elastomeric block copolymer having at least one hard block and at least one soft block, a macro photoinitiator, a processing oil, and optionally, a thermoplastic polymer and/or a crosslinking agent contain such a precursor. The weight average molecular weight of the low molecular weight elastomers or elastomeric precursors is between about 45,000 and about 150,000.

Suitable elastomeric compositions for use in the processes disclosed above may exhibit a wide range of melt viscosities as determined by the Melt Viscosity Test. As shown in the examples provided below and in FIG. 5, melt viscosities in excess of 10,000 Pa·s are clearly feasible. One skilled in the art would recognize that elastomeric compositions of lesser viscosity (i.e., less than 10,000 Pa·s) are equally feasible for the processes of the present invention. As a result, it should be understood that every viscosity and range of viscosities is included as if such viscosity or range of viscosities was expressly written herein.

Suitable elastomeric compositions for use herein form elastomeric members that are elastic without further treatment. Generally, these elastomeric compositions do not include any volatile solvents with boiling point below 150° C. After the elastomeric composition has been applied to the substrate, however, post-treatments may be used to improve or enhance the elasticity and other properties including strength, modulus, and the like of the resulting elastomeric members. Typically, post-treatments converting the elastomeric compositions into elastomeric members by methods such as cooling; heating; crosslinking; curing via chemical, thermal, radiation means; pressing between nip rolls, and combinations thereof.

EXAMPLES

A suitable elastomeric composition may be prepared by blending varying amounts of a styrenic elastomeric copolymer such as Vector® 4211, a styrene-isoprene-styrene block copolymer (SIS) from Dexco Company, Houston, Tex.; Low Molecular Weight SIS (LMW S-I-S) from Dexco Company, Houston, Tex.; Septon® 4033, a styrene-ethylene-ethylene/propylene-styrene block copolymer (SEEPS), from Septon Company of America, Pasadena, Tex.; a vinylarene resin such as polystyrene PS3900 from Nova Chemical, Inc. Moon Township, Pa.; a macro photoinitiator from National Starch and Chemicals, Bridgewater, N.J.; and mineral oil such as Drakeol® available from Penreco, Houston, Tex.

The appropriate amount of each component by weight percent of the elastomeric composition is added into a twin-screw extruder for both compounding and printing. In another approach, the elastomeric composition is pre-compounded to form a single pellet material. GLS Corporation of McHenry, Ill. is a suitable compounder for this operation. The single pellet material can be extruded for printing.

Examples of an elastomeric composition suitable for use herein are shown in Table 1. The approximate amount of each component is expressed as weight percent of the total elastomeric composition. Additives, including, for example, antioxidants and opacifiers, which are present only in small amounts, are not shown in the formulations presented in Table 1. Typically, the elastomeric compositions useful in the present invention comprise about 0.5 wt % of antioxidants, about 0.3 wt % of light stabilizers and about 3.0 wt % titanium dioxide.

TABLE 1

Elastomeric Compositions (Weight Percent)

| | Example 1 | Example 2 | Example 3 |
|---|---|---|---|
| S-I-S | 0 | 70 | 35 |
| LMW S-I-S | 0 | 0 | 20 |
| SEEPS | 55 | 0 | 0 |
| Polystyrene PS3900 | 15 | 5 | 0 |
| Mineral Oil | 30 | 25 | 40 |
| Macro-photoinitiator | 0 | 0 | 5 |

Test Method

Melt Viscosity Test

A 152 mm×152 mm aluminum mold plate containing a circular inset of 25 mm in diameter and 1.5 mm in thickness is used to prepare circular disks for the melt viscosity test. Approximately 3.0 grams of elastomeric composition (e.g., Example 1, 2, or 3) is placed in the 25 mm inset which is sitting on a sheet of Teflon. Another sheet of Teflon is placed on top of the sample/aluminum plate. A press containing heating plates, such as the Hydraulic Unit Model # 3925 available from Carver, Inc., Wabash, Ind. or another similar press, is pre-heated to a desired temperature sufficient to melt the elastomeric composition or to induce flow of the elastomeric composition. Generally, temperatures ranging from 150° C. up to 275° C. are sufficient. The mold along with Teflon sheets are placed in the Carver press for approximately one minute before closing the Carver press and applying a pressure of approximately 10,000 Psi for approximately 20 seconds. The pressure is released and the sample disk is removed from the mold. The sample disk is inspected (e.g., inspection with the unaided eye, excepting standard corrective lenses, in standard lighting conditions) for defects such as, for example, air bubbles. Samples with defects present may not be tested; however, the sample may be re-heated and re-pressed to remove the defect.

The melt viscosity of elastomeric compositions can be measured using an AR1000N Rheometer available from TA Instruments, New Castle, Del. or similar rheometer. The AR1000N may be equipped an Environmental Temperature Chamber (ETC), 25 mm hard anodized (HA) aluminum parallel plates, and a nitrogen purge. The rheometer may be interfaced with a computer loaded with software that controls the test conditions, records experimental data, and performs necessary analysis. A suitable computer for interface with the rheometer is the Dell Optiplex GX260 Pentium 4 Computer equipped with the Microsoft Windows XP Professional operating system. A suitable software includes Rheology Advantage Instrument Control AR, product version 4.0.1, file version 4.0.17 and Rheology Advantage Data Analysis, product version 4.0.23, file version 4.0.23; both available from TA Instruments. Calibration, sample handling and operation of the instrument may be conducted by following the manufacturer's operating procedure which are provided in an electronic format for the specific product version and file version as noted above. Modifications to the manufacturer's operating procedure are as disclosed herein.

Figure 5:
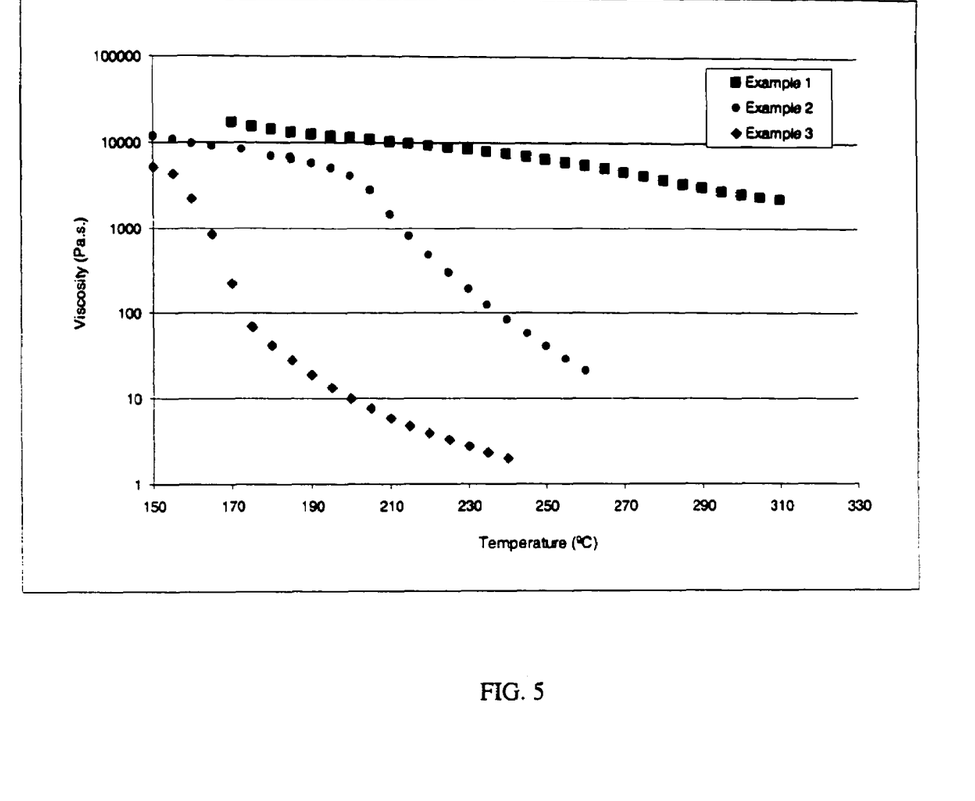
FIG. 5 is a graph plotting viscosity as a function of temperature for three formulations of the elastomeric composition.

The sample is placed between the rheometer's two 25 mm diameter parallel plates with an initial gap of 1.5 mm between the plates. The sample chamber is heated to 150° C. until it is equilibrated and the sample reaches 150° C. The gap is reduced to 1.0 mm. The melt viscosity is measured under temperature sweep test as described below:

Start Temperature: 150° C.
Final Temperature: 300° C.
Temperature Increment: 5° C.
Strain: 5%
Frequency: 1 radians/sec
Log Mode
Gap-1000 μm During the sweep, temperature change and data collection are done incrementally. The sample chamber is heated to the prescribed temperature (e.g., 150° C., 155° C., 160° C., and so forth to 300° C.). Once the sample reaches the prescribed temperature, a one minute delay occurs and then data is collected. The sample chamber is heated to raise the sample chamber temperature by an increment of 5° C. and the process is repeated. The resulting data for Examples 1, 2, and 3 are shown in the graph of FIG. 5 as function of viscosity (Pa·s) versus temperature (° C.).

Suitable uses for the corrugated stretch laminates that result from the processes of the present invention include use within disposable articles. Exemplary disposable articles include diapers, training pants, adult incontinence articles, sanitary napkins, garments like gloves, aprons, smocks, socks, etc. Exemplary disposable article construction is described generally in U.S. Pat. Nos. 3,848,594; 3,860,003; 4,662,875; 4,846,815; 4,894,060; 4,946,527; 5,151,092; 5,221,274; 5,554,145; 5,569,234; 5,580,411; 6,004,306; and 6,432,098 and in U.S. application Ser. No. 10/764,850. The disposable articles described in these patents and applications may comprise a variety of elements that require elastic regions. Such elements include, for example, ears, leg cuffs, waist bands, back panels, front panels, side panels, topsheets, fastener systems (e.g., tape tabs, hook and loop fastening components, interlocking fasteners such as tabs & slots, buckles, buttons, snaps, and/or hermaphroditic fastening components, and any other known fastening means), and combinations thereof. Elastic regions may comprise the corrugated stretch laminates that are manufactured via the process of the present invention. Furthermore, U.S. application Ser. No. 60/557,288 describes an absorbent article that comprises at least one stretch zone wherein the stretch zone comprises an elastomeric composition. The corrugated stretch laminate resulting from the present invention may be used to provide such stretch zones.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a corrugated stretch laminate, said process comprises the steps of:
    a) delivering a curtain of a first elastomeric composition in a molten state from a delivery mechanism directly to a grooved surface of a print device selected from the group consisting of gravure rolls and gravure webs, the grooved surface including a plurality of grooves adapted to receive the curtain of the first elastomeric composition in the molten state, wherein the first elastomeric composition exhibits a melt viscosity of greater than about 10,000 Pa·s at 175° C.;
    b) distributing the curtain of the first elastomeric composition into the plurality of grooves with a doctor blade;
    c) cooling the first elastomeric composition on the grooved surface of the print device to form an elastic member comprising an apertured film;
    d) removing the elastic member from the print device;
    e) elongating the elastic member in a first direction;
    f) joining the elastic member to a first substrate; and
    g) allowing the elastic member to recover to form said corrugated stretch laminate.

2. The process of claim 1 wherein the first direction is machine direction or cross-machine direction.

3. The process of claim 1 further comprising a step of treating the first elastomeric composition, wherein said treating is selected from the group consisting of crosslinking, curing, drying, cooling, heating, and combinations thereof.

4. The process of claim 1 wherein the first elastomeric composition is selected from the group consisting of styrenic block copolymers, polyolefins, polyesters, polyurethanes, polyether amides, and combinations thereof.

5. The process of claim 1 wherein the step of elongating the elastic member is performed by a device selected from the group consisting of Mount Hope rolls, off-speed rolls, tentering frames, angled idlers, angled nips, slatted spread rollers, edge pull web stretchers, and combinations thereof.

6. The process of claim 1 further comprising a step of joining the elastic member to a second substrate.

7. The process of claim 1 wherein said elastomeric composition comprises:
    a) from about 20 to about 100 wt% of a thermoplastic elastomer which is a block copolymer having at least one hard block comprising vinylarenes and at least one soft block comprising dienes;
    b) from about 0 to about 60 wt% of a processing oil; and
    c) from about 0 to about 60 wt% of at least one vinylarene resin.

8. The process of claim 1 further comprising a step of joining the corrugated stretch laminate into an absorbent article.

9. The process of claim 8 wherein said corrugated stretch laminate is provided in an element of the absorbent article selected from the group consisting of a waist feature, a cuff, a side panel, an ear, a backsheet, a topsheet, a fastener system, and combinations thereof.

10. The process of claim 1 wherein the elastic member is in a form selected from the group consisting of a film, an apertured film, a strand, a ribbon, or combinations thereof.

11. The process of claim 1 wherein the step of removing the elastic member from the print device comprises depositing the elastic member onto a conveying device.

12. The process of claim 11 wherein the conveying device is selected from the group consisting of a conveyor belt, a conveyor web, or a rotating cylinder.

13. The process of claim 1 wherein the step of removing the elastic member from the print device is performed such that the elastic member is self-supporting.

14. The process of claim 1 further comprising the steps of:
    a) delivering a second elastomeric composition to second print device to form a second elastic member;
    b) removing the second elastic member from the second print device;
    c) elongating the second elastic member in a second direction; and
    d) joining the second elastic member to the first substrate.

15. The process of claim 14, wherein said first elastic member and said second elastic member differ in a property selected from the group consisting of elasticity, melt viscosity, shape, pattern, add-on level, formulation, and combinations thereof.

16. A process for making a corrugated stretch laminate comprising the steps of:
    a) heating a first elastomeric composition to a first temperature, said temperature being sufficient to render the first elastomeric composition fluid or molten, wherein the elastomeric composition exhibits a melt viscosity of greater than about 10,000 Pa·s at 175° C.;
    b) delivering a curtain of the first elastomeric composition from a curtain coater directly onto an exterior surface of a gravure roll, the exterior surface interspersed with one or more cavities;
    c) distributing the curtain of the first elastomeric composition into the one or more cavities with a doctor blade;

d) cooling the first elastomeric composition below the first temperature to form an elastic member comprising an apertured film;
e) removing the elastic member from the gravure roll;
f) elongating the elastic member in a first direction;
g) joining the elastic member to a first substrate; and
h) allowing the elastic member to recover to form said corrugated stretch laminate.

17. The process of claim 1, wherein the delivery mechanism comprises an extruder.

* * * * *